US00PP20065P2

(12) United States Plant Patent
Henny et al.

(10) Patent No.: US PP20,065 P2
(45) Date of Patent: Jun. 9, 2009

(54) ***MANDEVILLA* PLANT NAMED 'GEM06-1'**

(50) Latin Name: ***Mandevilla* hybrid**
Varietal Denomination: GEM06-1

(75) Inventors: Barbara K. Henny, Tavares, FL (US); Richard J. Henny, Tavares, FL (US)

(73) Assignee: Gem Ornamentals, Inc., Tavares, FL (US)

( * ) Notice: Subject to any disclaimer, the term of this patent is extended or adjusted under 35 U.S.C. 154(b) by 0 days.

(21) Appl. No.: 12/154,222

(22) Filed: May 21, 2008

(51) Int. Cl.
*A01H 5/00* (2006.01)

(52) U.S. Cl. ..... Plt./232

(58) Field of Classification Search ..... Plt./232
See application file for complete search history.

*Primary Examiner*—Annette H Para
(74) *Attorney, Agent, or Firm*—C. A. Whealy

(57) ABSTRACT

A new and distinct cultivar of *Mandevilla* plant named 'GEM06-1', characterized by its upright, outwardly spreading and vining plant habit; moderately vigorous growth habit; large, smooth, shiny and dark green-colored leaves; thick stems; white-colored flowers with distinct yellow orange-colored centers; flowers with imbricate petals with ruffled margins; and good garden performance.

1 Drawing Sheet

Botanical designation: *Mandevilla* hybrid.
Cultivar denomination: 'GEM06-1'.

BACKGROUND OF THE INVENTION

The present invention relates to a new and distinct cultivar of *Mandevilla,* botanically known as *Mandevilla* hybrid and hereinafter referred to by the name 'GEM06-1'.

The new *Mandevilla* is a product of a planned breeding program conducted by the Inventors in Tavares, Fla. The objective of the breeding program is to create new *Mandevilla* cultivars with attractive plant form, vigor and flower coloration.

The new *Mandevilla* originated from a cross-pollination made by the Inventors in May, 2005 in Tavares, Fla. of *Mandevilla* hybrid 'Jumbo Blush', disclosed in U.S. Plant Pat. No. 10,095, as the female, or seed parent with an unnamed selection of *Mandevilla boliviensis,* not patented, as the male, or pollen, parent. The new *Mandevilla* was discovered and selected by the Inventors as a flowering plant from within the progeny of the stated cross-pollination in a controlled greenhouse environment in Tavares, Fla. on Jun. 6, 2006. The new *Mandevilla* was selected on the basis of its shiny dark green-colored foliage, good vigor and attractive flower coloration.

Asexual reproduction of the new cultivar by cuttings in Tavares, Fla., since June, 2006, has shown that the unique features of this new *Mandevilla* are stable and reproduced true to type in successive generations.

SUMMARY OF THE INVENTION

Plants of the new *Mandevilla* have not been observed under all possible environmental conditions. The phenotype may vary somewhat with variations in environment such as temperature and light intensity without, however, any variance in genotype.

The following traits have been repeatedly observed and are determined to be the unique characteristics of 'GEM06-1'. These characteristics in combination distinguish 'GEM06-1' as a new and distinct cultivar of *Mandevilla:*

1. Upright, outwardly spreading and vining plant habit.
2. Moderately vigorous growth habit.
3. Large, smooth, shiny and dark green-colored leaves.
4. Thick stems.
5. White-colored flowers with distinct yellow orange-colored centers.
6. Flowers with imbricate petals with ruffled margins.
7. Good garden performance and tolerant to low and high temperatures.

Plants of the new *Mandevilla* can be compared to plants of the female parent, 'Jumbo Blush'. In side-by-side comparisons conducted in Tavares, Fla., plants of the new *Mandevilla* differed from plants of 'Jumbo Blush' in the following characteristics:

1. Plants of the new *Mandevilla* were more vigorous than plants of 'Jumbo Blush'.
2. Plants of the new *Mandevilla* were more freely branching than plants of 'Jumbo Blush'.
3. Plants of the new *Mandevilla* and 'Jumbo Blush' differed in flower color as plants of 'Jumbo Blush' had pale pink-colored flowers with bright red purple-colored centers.

Plants of the new *Mandevilla* can be compared to plants of the male parent selection. In side-by-side comparisons conducted in Tavares, Fla., plants of the new *Mandevilla* differed from plants of the male parent selection in the following characteristics:

1. Plants of the new *Mandevilla* had thicker stems than plants of the male parent selection.
2. Plants of the new *Mandevilla* had larger leaves than plants of the male parent selection.
3. Plants of the new *Mandevilla* had larger flowers than plants of the male parent selection.

Plants of the new *Mandevilla* can be compared to plants of *Mandevilla* 'White Delite', disclosed in U.S. Plant Pat. No. 8,479. In side-by-side comparisons conducted in Tavares, Fla., plants of the new *Mandevilla* differed from plants of 'White Delite' in the following characteristics:

1. Plants of the new *Mandevilla* were more vigorous than plants of 'White Delite'.
2. Plants of the new *Mandevilla* had thicker stems than plants of 'White Delite'.
3. Plants of the new *Mandevilla* had larger leaves than plants of 'White Delite'.
4. Plants of the new *Mandevilla* and 'White Delite' differed in flower color as flowers of plants of 'White Delite' were initially pink in color.

Plants of the new *Mandevilla* can be compared to plants of *Mandevilla* 'White Velvet', disclosed in U.S. Plant Pat. No. 18,012. In side-by-side comparisons conducted in Tavares Fla., plants of the new *Mandevilla* differed from plants of 'White Velvet' in the following characteristics:

1. Plants of the new *Mandevilla* had thicker stems than plants of 'White Velvet'.
2. Plants of the new *Mandevilla* and 'White Velvet' differed in flower shape.
3. Plants of the new *Mandevilla* and 'White Velvet' differed in flower color as flowers of plants of 'White Velvet' were white and faintly overlain with red purple in color.

Plants of the new *Mandevilla* can also be compared to plants of *Mandevilla* 'Sunmandeho', disclosed in U.S. Plant Pat. No. 11,556. In side-by-side comparisons conducted in Tavares, Fla., plants of the new *Mandevilla* differed from plants of 'Sunmandeho' in the following characteristics:

1. Plants of the new *Mandevilla* had thicker stems than plants of 'Sunmandeho'.
2. Plants of the new *Mandevilla* had larger leaves than plants of 'Sunmandeho'.
3. Plants of the new *Mandevilla* and 'Sunmandeho' differed in flower shape.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the actual colors of the new *Mandevilla*. The photograph is a close-up view of a typical flowering plant of 'GEM06-1'.

DETAILED BOTANICAL DESCRIPTION

In the following description, color references are made to The Royal Horticultural Society Colour Chart, 1995 Edition, except where general terms of ordinary dictionary significance are used. Plants used for the aforementioned photograph and following description and observations were grown under conditions which closely approximate commercial production conditions during the spring and summer in a polyethylene-covered greenhouse in Tavares, Fla. in three-gallon containers. During the production of the plants, day temperatures ranged from 32° C. to 35° C. and night temperatures averaged 21° C. Plants used for the photograph and description were nine months old.

Botanical classification: *Mandevilla* hybrid 'GEM06-1'.

Parentage:

*Female, or seed, parent.*—*Mandevilla* hybrid 'Jumbo Blush', disclosed in U.S. Plant Pat. No. 10,095.

*Male, or pollen, parent.*—Unnamed selection of *Mandevilla boliviensis,* not patented.

Propagation:

*Type.*—By single node cuttings.

*Time to initiate roots, summer.*—About 16 days at 24° C.

*Time to initiate roots, winter.*—About 22 days at 21° C.

*Time to produce a rooted young plant, summer.*—About 45 days at 32° C.

*Time to produce a rooted young plant, winter.*—About 60 days at 12° C. to 27° C.

*Root description.*—Thick, fibrous.

*Rooting habit.*—Freely branching; moderately dense.

Plant description:

*Form/plant habit.*—Perennial evergreen flowering plant; twining vine. Plants initially upright and outwardly spreading, then vining, requiring support to maintain upright habit. Plants are typically pinched about six weeks and three months after planting to enhance lateral branch development; potentially two lateral branches form at every node. Moderately vigorous growth habit.

*Plant height* (*length*).—About 60 cm.

*Plant diameter* (*spread*).—About 50 cm.

*Lateral branch description.*—Length: About 40 cm. Diameter: About 4 mm. Internode length: About 6 cm. Strength: Flexible, moderately strong. Texture, developing stems: Fine pubescence. Texture, mature stems: Smooth, glabrous; woody. Color, developing stems: Close to 145A becoming closer to 146C with development. Color, mature stems: Close to 199D.

Foliage description:

*Arrangement.*—Opposite, simple.

*Length.*—About 12 cm to 14 cm.

*Width.*—About 7 cm to 8 cm.

*Shape.*—Elongated oblong.

*Apex.*—Sharply acute.

*Base.*—Cordate.

*Margin.*—Entire.

*Texture, upper and lower surfaces.*—Fine pubescence.

*Luster, upper surface.*—Glossy.

*Luster, lower surface.*—Somewhat glossy.

*Venation pattern.*—Pinnate.

*Color.*—Developing and fully expanded foliage, upper surface: More green than 147A; venation, close to 139D. Developing and fully expanded foliage, lower surface: Close to 146A; midvein, close to 139D; lateral veins, close to 139A.

*Petiole length.*—About 1.5 cm.

*Petiole diameter.*—About 2 mm.

*Petiole texture, upper and lower surfaces.*—Pubescent.

*Petiole color, upper surface.*—Close to 146B.

*Petiole color, lower surface.*—Close to 146D.

Flower description:

*Flower type and habit.*—Single salverform flowers; flowers arranged on axillary or terminal racemes; flowers face mostly outward. Freely flowering habit, about 20 flowers develop per plant during the flowering season.

*Natural flowering season.*—Plants of the new *Mandevilla* flower continuously from spring until frost in the autumn in Tavares, Fla.

*Flower longevity on the plant.*—About three to five days. Flowers not persistent.

*Fragrance.*—None detected.

*Flowers.*—Appearance: Flared trumpet, corolla fused, five-parted; petal apices curve downward towards the corolla base. Diameter: About 8 cm. Depth (length): About 5 cm. Corolla throat diameter: About 1.5 cm. Corolla tube length: About 2.5 cm. Corolla tube diameter (at the base): About 3.5 mm.

*Flower buds* (*just before opening*).—Length: About 6 cm. Diameter: About 1.5 cm. Shape: Elongated oblong. Color: Close to 157A.

*Corolla.*—Arrangement/appearance: Single whorl of five imbricate petals, fused into flared trumpet. Petal lobe length: About 3 cm. Petal lobe width: About 3.5 cm. Petal shape: Roughly spatulate. Petal apex: Rounded; undulate and ruffled in appearance. Petal margin: Entire; undulate and ruffled in appearance. Petal texture, upper and lower surfaces: Smooth, glabrous; velvety. Color: Petal, when opening and fully opened, upper surface: Close to 155D. Petal, when opening and fully opened, lower surface: Close to 155D. Corolla tube: Close to 150C. Corolla throat: Towards the base, close to 17A; towards the petal lobes, close to 12C.

*Sepals.*—Arrangement/appearance: Five per flower in a single whorl; fused at the base; reflexed. Length: About 1 mm. Width: About 2 mm. Shape: Deltoid. Apex: Acuminate. Margin: Entire. Texture, upper and lower surfaces: Smooth, glabrous; slightly waxy. Color, upper and lower surfaces: Close to 144B.

*Peduncles.*—Length: About 2.5 cm. Diameter: About 2 mm. Texture: Smooth, glabrous. Strength: Flexible, but strong. Color: Close to 144A.

*Reproductive organs.*—Stamens: Quantity/arrangement: Typically five; filaments fused to corolla; anthers, connivent. Anther shape: Elongated oblong. Anther size: About 8 mm by 1.5 mm. Anther color: Close to 11A. Pollen amount: Scarce. Pollen color: Close to 11A. Pistils: Quantity: Typically one. Pistil length: About 1.9 cm. Stigma shape: Rounded. Stigma color: Close to 150D. Style color: Close to 155D. Ovary color: Close to 144A to 144B.

*Seed/fruit.*—Seed and fruit production has not been observed.

Disease/pest resistance: Plants of the new *Mandevilla* have not been noted to be resistant to pathogens and pests common to *Mandevilla.*

Garden performance: Plants of the new *Mandevilla* have been observed to have good garden performance and to tolerate rain, wind and temperatures ranging from about 0° C. to about 40°C.

It is claimed:

1. A new and distinct *Mandevilla* plant named 'GEM06-1' as illustrated and described.

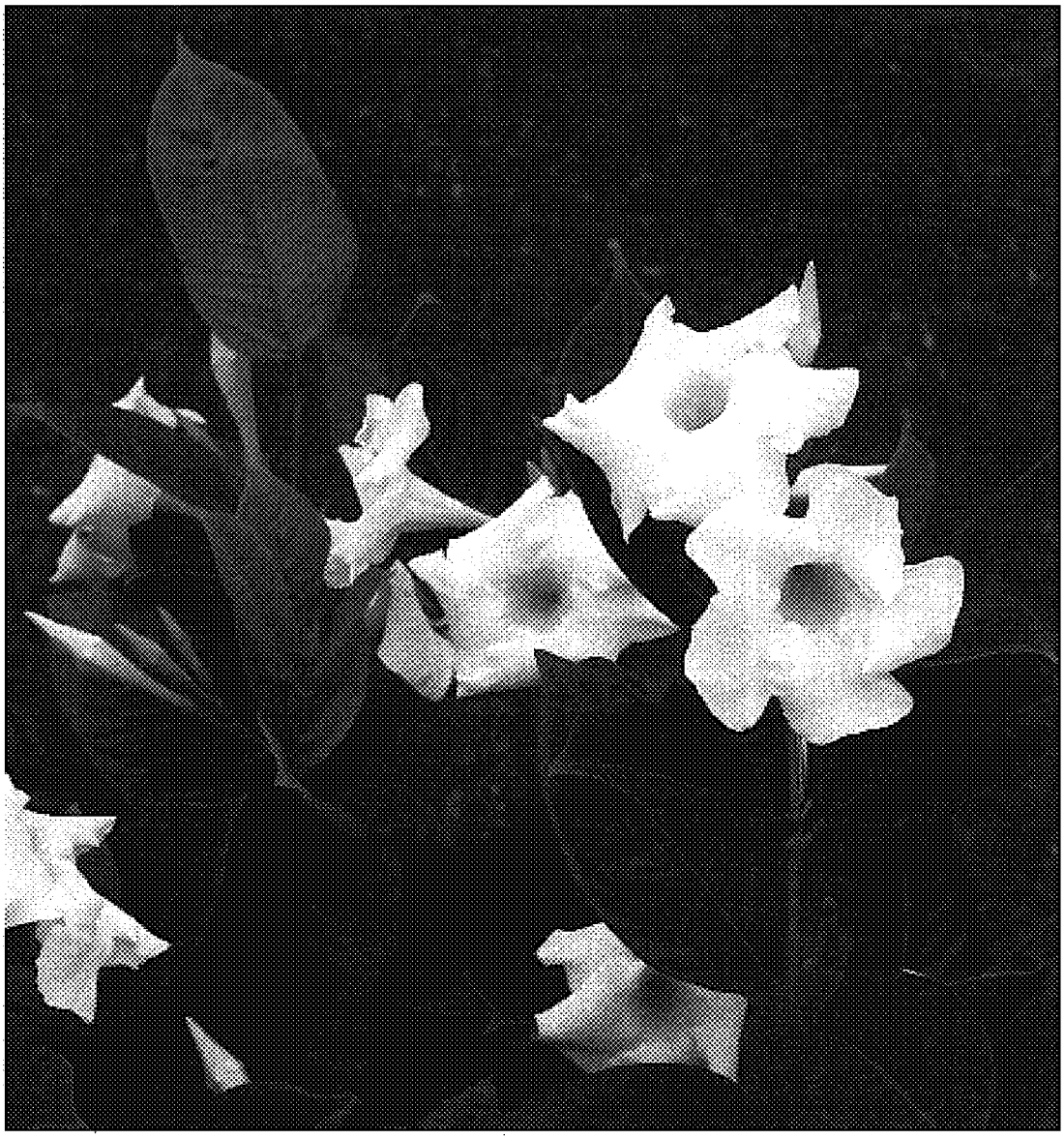

* * * * *